United States Patent
Love et al.

(10) Patent No.: US 6,642,010 B2
(45) Date of Patent: Nov. 4, 2003

(54) IDENTIFYING, MONITORING, AND TREATING WOMEN FOR BREAST PRECANCER OR CANCER

(75) Inventors: Susan Love, Pacific Palisades, CA (US); David Hung, Belmont, CA (US); Hui Cen, Oakland, CA (US)

(73) Assignee: Cytyc Health Corporation, Boxborough, MA (US)

(*) Notice: Subject to any disclaimer, the term of this patent is extended or adjusted under 35 U.S.C. 154(b) by 8 days.

(21) Appl. No.: 09/502,404

(22) Filed: Feb. 10, 2000

(65) Prior Publication Data

US 2003/0022161 A1 Jan. 30, 2003

Related U.S. Application Data

(63) Continuation-in-part of application No. 09/313,463, filed on May 17, 1999.
(60) Provisional application No. 60/117,281, filed on Jan. 26, 1999.

(51) Int. Cl.$^7$ .............................................. G01N 33/574
(52) U.S. Cl. ....................... 435/7.23; 435/7.1; 435/7.21
(58) Field of Search ....................... 424/199.1; 436/63; 435/7.1, 7.21, 7.23

(56) References Cited

U.S. PATENT DOCUMENTS

| | | | |
|---|---|---|---|
| 4,202,329 A | 5/1980 | Kortum | |
| 4,365,632 A | 12/1982 | Kortum | |
| 4,981,692 A | 1/1991 | Popescu et al. | |
| 5,279,608 A | 1/1994 | Cherif Cheikh | |
| 5,531,736 A | 7/1996 | Wong et al. | |
| 5,763,415 A | 6/1998 | Sukumar | |
| 5,798,266 A | 8/1998 | Quay et al. | |
| 5,840,059 A | 11/1998 | March et al. | |

FOREIGN PATENT DOCUMENTS

WO    WO 97/05898    2/1997

OTHER PUBLICATIONS

Medline accession No. 95312799 (1995).*
King et al JNCI, vol. 71 p. 1115 (1983).*
Fabian et al J. Cell. Biochem. vol. 17G p. 153 (1993).*
Hou et al Radiology vol. 195 p. 568 (1995).*
Grady et al, Annals of Internal Medicine vol. 117 p. 1016 (1992).*
Orcel, La Revue Du Practicien, vol. 45 p. 1107 1995.*
Fabien, et al., 1993, Journal of Cellular Biochemistry, 17G:153–160.*
Brodie, et al., 1998, Breast Cancer Research and Treatment, 49:S85–S91.*
Sartorius, et al., 1997, J. Natl. Cancer Inst., 59:(4), 1073–1080.*
Fisher et al., "Tamoxifen for prevention of breast cancer: Report of the National Surgical Adjuvant breast and bowel project P–1 study" *Journal of the National Cancer Institute* (1998)*90*(18):1371–1388.
Goodson et al., "Discharges and secretions of the nipple" *The Breast: Comprehensive Management of Benign & Malignant Diseases*, Bland & Kirby, Eds., W.B. Saunders, Philadelphia, Second Edition, Chapter 4, (1998) 2:51–74.
Hou et al., "A simple method of duct cannulation and localization for galactography before excision in patients with nipple discharge" *Radiology* (1995) *195*:568–569.
King et al., "Nipple aspirate cytology for the study of breast cancer precursors" *Journal of the National Cancer Institute* (1983) *71*:1115–1121.
Love et al., "Breast–duct endoscopy to study stages of cancerous breast disease" *The Lancet* (1996) *348*:997–999.
Papanicolaou et al., "Exfoliative cytology of the human mammary gland and its value in the diagnosis of cancer and other diseases of the breast:" *Cancer* (1958) *11*(2):377–409.
Pansera, F., "Accessibility and possibility of elimination of breast epithelium: The theoretical possibility of preventing breast carcinoma through destruction of the epithelium of origin" *Medical Hypothesis* (1990) *33*:107–111.
Sartorius et al., "Cytologic evaluation of breast fluid in the detection of breast disease" *Journal of the National Cancer Institute* (1977) *59*(4):1073–1078.
Sauter et al., "Nipple aspirate fluid: A promising non–invasive method to identify cellular markers of breast cancer risk" *British Journal of Cancer* (1997) *76*(4):494–501.
Wrensch et al., "Breast cancer incidence in women with abnormal cytology in nipple aspirates of breast fluid" *American Journal of Epidemiology* (1992) *135*(2):130–141.
"PAP Test for Breast Cancer" newspaper clipping regarding Dr. Sartorius.
Barnes & Masood. "Potential value of hormone receptor assay in carcinoma in situ of breast" AJCP 11/90.
Berntsen, et al. "Influence of Treatment with Aminoglutethimide on Plasma and Red–Blood–Cell Glutathione Status in Breast Cancer Patients." Cancer Chemother Pharmacol. 1998. vol. 42, pp. 46–52.

(List continued on next page.)

*Primary Examiner*—Sheela Huff
(74) *Attorney, Agent, or Firm*—Banner & Witcoff, Ltd.

(57) ABSTRACT

The invention is to methods for screening women for breast cancer and precancer by determining a level of an estrogen-related marker. The invention further provides methods of treating such patients identified as having one or more abnormal ductal epithelial cells and an estrogen-related marker. The invention provides methods for screening patient for hormone replacement therapy (HRT), and of monitoring such patients once they begin HRT. The invention provides methods of treating peri-, menopausal or postmenopausal women for both cancer risk reduction and menopausal symptoms (or other conditions related to lowered systemic estrogen levels). The invention also provides kits for the screening, monitoring, and treating methods described.

17 Claims, No Drawings

OTHER PUBLICATIONS

Boccuzzi, et al. "Breast Duct Fluid Dehydroepiandrosterone sulphate in Fibrocystic Disease." European J. Cancer and Clinical Oncology. Aug. 1987. vol. 23, pp. 1099–1102.

"Cancer detection techniques shown." Santa Barbara News Press Aug. 3, 1971, newspaper clipping.

Ernster, et al. "Benign and malignant breast disease: initial study results of serum and breast fluid analyses of endogenous estrogens." JNCI vol. 79 No. 5.

Fabian, et al. "Biomarker and cytologic abnormalities in women at high and low risk for breast cancer" J of Cellular Biochemistry 17G:153–160 (1993).

"Finding asymptomatic breast cancer." Medical World News Jul. 23, 19719.

Fryckberg, et al. "Ductal carcinoma in situ of the breast." Surgery, Gynecology & Obstetrics 10/93 vol 177.

Kristensen et al. "A rare CYP19 (aromatase) variant may increase the risk of breast cancer." Pharmacogenetics. 1998. vol. 8, pp. 43–48.

Lobsenz. "A new way to detect breast cancer early." Good House Keeping Jan 1975.

Lu et al. "The Effects of Aromatase Inhibitors and Antiestrogens in the Nude Mouse Model." Breast Cancer Research and Treatment 1998. vol 50, pp. 63–71.

Masood, et al. "Breast health Challenges and Promises." J. Florida M.A. Aug./Sep. 1996/vol. 83, No. 7 pp. 459–465.

Masood. Fluorescent cytochemical detection of estrogen and progesterone receptors in breast fine–needle aspirates. AJCP 1/91.

Masood. "The missing link: a pap smear" for early breast cancer detection and prevention. The Breast Journal, vol 5 No. 1, 1999 pp. 1–2.

Nass, et al. "Breast cancer biology blossoms in the clinic." Nature Medicine vol 4 No. 7 Jul. 1998.

Pertshuk, et al. "Estrogen receptor immunochemistry in endometrial carcinoma." Gynecologic oncology 63, 28–33 (1996) pp. 28–33.

Petrakis & King. "Genetic markers and cancer epidemiology." Cancer Apr. supp 1977 vol 39 pp1861–1866.

Petrakis et al. "Epithelial dysplasia in nipple aspirates of breast fluid: association with family history and other breast cancer risk factors." JNCI vol 68 No. 1 1/82.

Petrakis; "Nipple aspirate fluid in epidemiologic studies of breast disease." Epidemiologic reviews vol 15 No. 1 1993.

Rose, et al. "A Comparison of Serum and Breast Duct Fluid Immunoassayable prolactin and Growth Hormon Woman and and Patients with Cystic Breast Disease." Cancer, Dec. 1, 1987. vol 60. No. 11, pp. 2761–2765.

Sartorius, et al. "The Biochemistry of breast cyst fluids and duct secretions." Breast cancer research and Treatment 35:255–266 1995.

Sauter et al. "Prostate specific antigen levels in nipple aspirate fluid correlate with breast cancer risk" Cancer Epidemiology vol. 5, 967–970, Dec. 1996.

Schairer, et al, JAMA 2000; 283: 485–491.

Strah & Love. "The in situ carcinomas of the breast." JAMWA vol 47 No. 5 Sep./Oct. 1992.

Sukumar & McKenzie, "Breast cancer prevention strategies for the twenty–first century" Molecular Medicine Today 11/96.

Sukumar et al. "Independent Molecular Pathways in Initiation and Loss of Hormone responsiveness of breast carcinomas." Science Apr. 22, 1988.

Wynder et al, "Prolactin Oestrogen, and Lipids in Breast Fluid." Oct. 22, 1977. vol. 2 No. 8043, pp. 840–842.

Zippin & Petrakis, "Identification of high risk groups in breast cancer." Cancer vol 28 pp 1381–1387 Dec. 1971.

Petrakis, N.L., "Estrogen and Other Biochemical and Cytological Components in Nipple Aspirates of Breast Fluid Relationship to Risk Factors for Breast Disease", Proceedings of the Royal Society of Edinburgh Section B, vol. 95, pp. 169–182, 1989.

Bulin, S.E., et al, Endocrine Disorders Associated With Inappropriately High Aromatase Expression, The Journal of Steroid Biochemistry and Molecular Biology, England APR, vol. 61, Nos. 3–6, pp. 133–139, 1997.

Wynder, E.L. et al., "Prolactine, Oestrogen and Lipids in Breast Fluid", Lancet, vol. 2, No. 8043, pp. 840–842, Oct. 22, 1977.

King, E.B., et al., "Analytic Studies of Foam Cells From Breast Cancer Precursors", Cytometry, vol. 5, No. 2, pp. 124–130, Mar. 1984.

EPO 00 990 5775 Supplementary partial European Search Report, dated Feb. 26, 2003.

* cited by examiner

IDENTIFYING, MONITORING, AND TREATING WOMEN FOR BREAST PRECANCER OR CANCER

CROSS-REFERENCES TO RELATED APPLICATIONS

The present application is a continuation-in-part of U.S. application Ser. No. 09/313,463, filed on May 17, 1999, which claimed the benefit and priority of Provisional U.S. Application No. 60/117,281 filed on Jan. 26, 1999, under 37 CFR §1.78, the full disclosures of which are incorporated herein by reference.

BACKGROUND OF THE INVENTION

1. Field of the Invention

The field of this invention is identifying, treating and monitoring women at risk for or having breast precancer or cancer.

2. Description of the Background Art

The approximate age of menopause for women in the United States is 51, and the mean life expectancy of such women is 85 years; thus most American women will live a third of their lives without significant estrogen production. Estrogen supplementation was first used in 1935 to ameliorate menopausal symptoms, and a few years later findings indicated that estrogen supplementation had beneficial effects on osteoporosis associated with aging. Around 1966 menopause was declared a "curable disease" by taking estrogen supplements. In 1975 articles warned that continuous estrogen supplementation alone increased the risk of endometrial cancer. By early 1980s, a new synthetic estrogen was prescribed that negated the endometrial cancer risk. Thereafter, attention was turned to the advantages of estrogen on cardiovascular mortality. Presently, concerns of estrogen therapy still exist with regard to breast cancer, but the issue is debated, with some reports indicating a causal linkage and other reports not identifying such a concern. (Summarized from page 771 Danforth's *Obstetrics and Gynecology*, seventh edition, ed. Scott et al., JB Lippincott Co., Philadelphia, 1994.)

Although the role of hormone replacement therapy (HRT) using estrogen or an estrogen/progestin combination in the etiology of breast cancer continues to be debated (Colditz, G A *J. Women's Health* 8(3): 347–57 (1999), the magnitude of increase in breast cancer risk per year of hormone use is comparable to that associated with delaying menopause by a year (Colditz, G A *J. Nat'l Cancer Inst* 90(11): 814–23 (1998). Adding support to these conclusions is other research concluding that experimental and clinical evidence currently underway and recently completed suggests that breast neoplasia is a hormone-dependent process (Newman et al., *J. Surg. Oncol.* 71(4): 250–260 (1999)) and as such a postmenopausal patient may be placed at increased risk of breast neoplasia with prolonged HRT. Studies conducted by at least one group in Tavani and Vecchia, *Drugs Aging* 14(5): 347–57 (1999) indicate that there is a 2.3% risk of breast cancer for women on HRT for from 5 to 15 years if the women start the therapy at age 50. Estrogens and estrogen/progestin combination are most frequently prescribed to patients experiencing menopausal symptoms, and generally the duration of treatment is about a year but sometimes up to 5 years for these patients. Less frequently, estrogen is prescribed to postmenopausal women experiencing osteoporosis (bone density loss). The treatment duration for osteoporosis, a potentially serious and life threatening condition, can be prolonged. Osteoporosis is associated with increased mortality due to increased fractures, particularly hip fractures and affects millions of people worldwide. Women of postmenopausal age (i.e., approximately over 50 years of age) are one category prone to the development of low bone density associated with osteoporosis. See, Watts, *Obstet Gynecol Surv* 54(8): 532–8 (1999). Osteoporosis is reduced with estrogen administration. See, for example Shoupe D, *Hosp Pract (Off Ed)* 34(8): 97–103, 107–8, 113–4 (1999).

Estrogen administration has also positive effects to reduce the risk of cardiovascular risk in postmenopausal women. (See, for example Shoupe D, *Hosp Pract (Off Ed)* 34(8): 97–103, 107–8, 113–4 (1999). There is evidence that estrogen therapy decreases risk for coronary heart disease (and for hip fracture), but long-term estrogen therapy increases risk for endometrial cancer and may be associated with a small increase risk for breast cancer (See, Grady, D et al., *Ann Intern Med* 117(12): 1016–37 (1992)).

Accordingly, taking into account the risks and benefits of estrogen administration it has been recommended that women diagnosed with breast cancer should use hormones sparingly to ameliorate menopausal symptoms (See, Colditz G A, *Oncology* 11(10): 1491–4, 1497, 1498, 1501 (1997). The call has also been made for alternatives to HRT for the long term prevention of heart disease and osteoporosis, See, Colditz G A, *Oncology* 11(10): 1491–4, 1497, 1498, 1501 (1997) and Ettinger, B *Proc Soc Exp Biol Med* 217:2–5 (1998), especially in view of research that indicates that long-term estrogen replacement therapy is associated with lower all-cause mortality and confers this apparent protection primarily through reduction in cardiovascular disease (See, Ettinger, B et al., *Obstet Gynecol* 87(1):6–12 (1996)). In general, postmenopausal hormone therapy may not be recommended for all postmenopausal women (See, Grady, D et al., *Ann Intern Med* 117(12): 1016–37 (1992) and Barrett-Connor E and Grady D, *Annu Rev Public Health* 19:55–72 (1998)).

Thus, given the great benefits of estrogen, but the established sensitivity of estrogen positive breast cancer lesions to estrogen stimulation, it would be prudent to develop sensitive screening and monitoring methods to provide postmenopausal women and their prescribing physicians information to make informed treatment choices in the best interest of the patient. The present invention provides these benefits.

Relevant Literature

Breast fluid was collected from nonlactating Finnish women with no known breast disease and analyzed for markers including estrogen; levels of estrogen in the fluid were six-fold higher than in the serum, Wynder et al., *Cancer* 47(6): 1444–50 (1981); and a possible correlation was made to the high levels of estrogen found in the ductal fluid of Western women and the development of breast cancer, Wynder and Hill *Lancet*, 2(8043): 840–2 (1977).

Estrogen (estrone and estradiol) levels were investigated (Petrakis et al., *Int J Cancer* 40(5): 587–91 (1987) in serum and nipple aspirates of breast fluid in relation to the reproductive and menopausal characteristics in 104 normal women; breast fluid and serum levels were not correlated; breast fluid estrogen levels were about 5 to 45 times higher than serum levels; serum estrogen levels were lower in postmenopausal women than premenopausal women; it was postulated that the high concentrations of estrogen in breast fluid and the absence of a relationship to serum estrogen levels may explain why serum studies have failed to link variations in serum estrogens with breast cancer risk.

Higher breast fluid E2 (estradiol) and E1 (estrone) levels were found in women with biopsied benign breast disease than in controls; but no evidence of a correlation of serum and breast fluid measurements was found. Ernster et al., *J Natl Cancer Inst* 79(5): 949–60 (1987).

Papanicolaou et al., (1958) *Cancer,* 11:377–409 describes exfoliative cytology from spontaneous nipple discharge of the human mammary gland and its value in the diagnosis of breast cancer. Goodson W H & King E B, *Chapter* 4: *Discharges and Secretions of the Nipple, The Breast: Comprehensive Management of Benign and Malignant Diseases* (1998) $2^{nd}$ Ed. Vol 2, Bland & Kirby eds. W.B. Saunders Co, Philadelphia, Pa. pp. 51–74 describes nipple discharge and the ways in which it has been used to characterized conditions of the breast.

Sartorius et al., (1977) proposed cytologic evaluation of breast fluid for the detection of breast disease as describe in *Journal of the National Cancer Institute* 59(4):1073–80. Love and Barsky, (1996) *Lancet* 348(9033):997–9 demonstrated retrieval of ductal fluid by breast-duct endoscopy to study stages of cancerous breast disease.

Nipple aspirate cytology for the study of breast cancer precursors is described in King et al., (1983) *Journal of the National Cancer Institute* 71(6):1115–21. Cytological epithelial hyperplasia and atypical hyperplasia diagnosed in nipple aspirate fluid are associated with increased risk of breast cancer in a study of 2701 women as 0described in Wrensch et al., (1992) *Am. J. Epidemiology,* v. 135 (2): 130–141.

Nipple aspirate fluid is identified as a promising noninvasive method to identify cellular markers of breast cancer risk in Sauter et al., (1997) *British Journal of Cancer* 76(4):494–501.

A company called Diagnostics, Inc. formed in 1968 produced devices to obtain breast ductal fluid for cytological evaluation. The devices included a nipple aspiration device to collect NAF from subjects, and catheters to retrieve ductal fluid. The devices were sold prior to May 28, 1976, for the purpose of collecting breast ductal fluid for cytological evaluation.

SUMMARY OF THE INVENTION

The invention provides a method of screening women for breast cancer or precancer comprising providing a ductal fluid sample from at least one duct of a breast of the patient and determining in the sample a level of a marker including aromatase enzyme, aromatase activity, a biproduct of estrogen synthesis and a protein effector acting upstream of estrogen synthesis; wherein a detectable level above a normal value indicates an increased risk for breast cancer or precancer. The method can further comprise detecting one or more precancerous or cancerous ductal epithelial cells in the sample; wherein the presence of precancerous or cancerous cells indicates that the patient has an increased chance of benefiting from administration of an estrogen activity modulator. Detecting can comprise detecting cells at a stage including ductal hyperplasia, atypical ductal hyperplasia, low grade ductal carcinoma in situ (LG-DCIS), high grade ductal carcinoma in situ (HG-DCIS) and invasive carcinoma. The method can comprise determining in the sample a level of estrogen or estrogen metabolite, wherein the level above normal indicates a risk for developing abnormal cells in the duct. The method can further comprise examining any abnormal cells to detect the presence of an estrogen receptor on the surface, wherein the presence of the estrogen receptor indicates that the cell is hormone responsive. The method can comprise detecting precancerous or cancerous ductal epithelial cells in the sample; wherein the presence of precancerous or cancerous ductal epithelial cells indicates that the patient has an increased chance of benefiting from at least one of administration of an estrogen activity modulator, stopping the HRT, reducing the dosage of hormone in the HRT, and/or switching to a different hormone or agent for treating menopausal symptoms or osteoporosis. The method can further comprise determining in the sample an elevated level of estrogen or estrogen metabolite, wherein a level above normal indicates an increase risk for developing cancer or precancer in the breast. The method can further include examining any abnormal cells to detect the presence of an estrogen receptor on the surface, wherein the presence of the estrogen receptor indicates that the cell is hormone responsive.

The invention further provides a method of treating a woman who has been determined to have one or more precancerous or cancerous ductal epithelial cells in a breast duct and an elevated level of a marker selected from the group consisting of aromatase enzyme, aromatase activity, a biproduct of estrogen synthesis, and a protein acting upstream of estrogen synthesis in a ductal fluid sample the method comprising administering at least one dose of an aromatase inhibitor to the woman. Another method of treating a woman who has been determined to have one or more or both of (a) precancerous or cancerous ductal epithelial cells in a breast duct, and (b) an increased level of estrogen or estrogen metabolite in a ductal fluid sample can comprise administering at least one dose of an estrogen activity modulator intraductally. The estrogen activity modulator can include an estrogen antagonist, an aromatase inhibitor, a selective estrogen receptor modulator, a modulator of a protein effector acting upstream of estrogen synthesis, and a cocktail of estrogen activity modulators.

The invention also provides a method of screening patients for postmenopausal hormone replacement therapy (HRT), the method comprising providing a ductal fluid sample from at least one duct of a breast of the patient, and examining the ductal fluid sample for the presence of a precancerous or cancerous ductal epithelial cell; wherein HRT is contradicted in patients having precancerous or cancerous ductal epithelial cells in the ductal fluid sample. The method can further comprise determining in the sample a level of a marker including an aromatase enzyme, aromatase activity, estrogen, estrogen metabolite, a biproduct of estrogen synthesis, or a protein acting upstream of estrogen synthesis in a ductal fluid, wherein a level above normal indicates an increased risk for developing cancer or precancer in the breast. The method can further comprise detecting precancerous or cancerous ductal epithelial cells in the sample, wherein the presence of precancerous or cancerous ductal epithelial cells indicates the patient has an increased chance of benefiting from at least one of administering a lower dosage of hormone in the HRT, close monitoring of markers and ductal epithelial cell changes while the patient is on HRT, selecting an agent for HRT that provides a reduced breast cancer risk, not placing the patient on HRT, and administering an estrogen activity modulator to an affected duct or ducts intraductally.

The invention also provides a method of monitoring a postmenopausal woman on hormone replacement therapy (HRT) comprising providing a ductal fluid sample from one or more ducts of a breast of a patient, and examining the ductal fluid sample for a precancerous or cancerous ductal epithelial cell, wherein indicated therapies for patients found to have precancerous or cancerous epithelial cells include stopping HRT, reducing a dosage of hormone in the HRT, taking an estrogen activity modulator systemically, taking an estrogen activity modulator intraductally, switching to a different drug to reduce menopausal symptoms, and switching to a different drug to reduce bone loss. When the action selected comprises taking an estrogen activity modulator, the estrogen activity modulator can be administered intraductally. The estrogen activity modulator can comprise an aromatase inhibitor. The method can further comprise assaying the ductal fluid for an elevated level of a marker including estrogen, an estrogen metabolite, aromatase enzyme, evidence of aromatase activity, biproducts of estrogen synthesis, or a protein effector acting upstream of estrogen synthesis; wherein indicated therapies for patients having an elevated level of one or more markers above normal include administration of a lower dosage of hormone in the HRT, close monitoring of markers while the patient is on HRT, close monitoring of ductal epithelial cell changes while the patient is on HRT, selecting an agent for HRT that provides a reduced cancer risk, stopping the HRT, or intraductal administration of an estrogen activity modulator to an affected duct or ducts. When a marker is elevated above normal, and the ductal epithelial cells are normal, the patient is directed to remain on HRT and be monitored periodically for changes in marker levels and ductal epithelial cell character.

The invention provides a method of treating a peri-, menopausal, or postmenopausal woman for both cancer risk and reduction of menopausal symptoms, osteoporosis, or cardiovascular risk wherein the peri-, menopausal, or postmenopausal woman has been found to have an elevated level of a marker including estrogen, an estrogen metabolite, aromatase enzyme, aromatase activity, a biproduct of estrogen synthesis, or a protein acting upstream of estrogen synthesis in a ductal fluid, the method comprising systemically administering estrogen hormone, and locally administering an estrogen activity modulator to breast milk ducts which display an elevated level of one or more markers. The estrogen activity modulator can comprise an estrogen antagonist, an aromatase inhibitor, or a cocktail of estrogen activity modulators. The estrogen activity modulator can be an aromatase inhibitor selected from the group consisting of toremifene, anastrozole, letrozole, fadrozole, lentaron, formestane and rivizor.

The invention provides also kits comprising a device for retrieving a ductal fluid sample from a breast duct and instructions for use setting forth a method according to any of claimed methods. The kits can further comprise a therapeutic agent for intraductal delivery to a patient, wherein the therapeutic agent comprises an estrogen activity modulator. The estrogen activity modulator can comprise an aromatase inhibitor.

DESCRIPTION OF THE SPECIFIC EMBODIMENTS

The following preferred embodiments and examples are offered by way of illustration and not by way of limitation.

The method of the invention provides a method of screening women at risk for breast cancer or precancer comprising providing a ductal fluid sample from at least one duct of a breast of the patient; and detecting an increased level of a certain marker wherein an increased level of one or more markers indicates an increased risk for breast cancer or precancer. The women can be any woman, and can thus be classified e.g., as pre-, peri-, menopausal, or postmenopausal. A pre-menopausal women age can be any woman squarely positioned well before menopause but after beginning menstruation. Peri-menopausal age is about 5 to 7 years before menopause. Menopause occurs for most women around age 50, plus or minus 2 or 3 years, and postmenopausal women are age from about age 50 onward, e.g., women who have completed menopause. The woman may have been previously diagnosed with breast cancer. The woman may be postmenopausal and on hormone replacement therapy (HRT). The marker is one or more estrogen-related markers, e.g., aromatase enzyme, aromatase activity, a biproduct of estrogen synthesis or a protein effector acting upstream of estrogen synthesis.

The method is practiced by providing a ductal fluid sample from at least one duct of a breast of the patient. Providing the ductal fluid sample can comprise obtaining the sample from the breast. Providing the ductal fluid sample can also comprise receiving a sample that had been previously obtained. For example, a laboratory can receive a ductal fluid sample from a patient or a practitioner, and the laboratory can be directed to make an analysis of the sample. Where the fluid is obtained from the breast, the fluid sample can be obtained e.g., by nipple aspiration of the milk ducts or by ductal lavage of at least one breast milk duct. When fluid is collected by nipple aspiration, or by ductal lavage, the fluid can be collected from a single duct. For example the duct and the collection tube can be marked so that the analysis of the fluid is traceable to one duct.

By the procedure of ductal lavage, ductal epithelial cells that line the walls of the ductal lumen are washed out of the duct. Lavage or wash fluid is infused into the duct, and the lavage fluid mixed with ductal fluid is collected. Lavage is described and claimed in copending and co-owned application Ser. Nos. 09/067,661, 09/301,058, PCT/US 99/09141, 60/122,076, 09/313,463, 60/143,359, and application Ser. No. 09/473,510, all incorporated by reference in their entirety. In some cases suction can be applied to the tool accessing the ductal lumen in order to retrieve a maximum amount of cells and/or fluid. Lavage or wash fluid can be infused into the duct, and collected. Suction can be applied to the tool accessing the ductal lumen in order to retrieve a maximum amount of cells and/or fluid. Access of a breast duct can be facilitated as described in e.g., Love & Barsky, (1996) *Lancet* 348: 997–999, Makita et al., (1991) *Breast Cancer Res Treat* 18: 179–188, or Okazaki et al., (1991) *Jpn J. Clin. Oncol.* 21:188–193. Alternatively, ductal fluid can be retrieved by a medical tool, e.g., a catheter or a cannula placed into the duct to infuse wash fluid to retrieve a mixture of wash and ductal fluids. The fluid from the breast duct can contain ductal epithelial cells, including cells of a stage considered to be precancerous or cancerous.

Nipple aspiration of breast ductal fluid is achieved by using vacuum pressure. Nipple aspiration techniques are also described and claimed in co-pending and co-owned patent application No. 60/108,449 and subsequently filed utility application attorney docket no. 18612-610 filed Nov. 12, 1999, both herein incorporated by reference in their entirety. Nipple aspirate fluid can be retrieved as described in e.g., Goodson W H & King E B, *Chapter 4: Discharges and Secretions of the Nipple,* The Breast: Comprehensive Management of Benign and Malignant Diseases (1998) $2^{nd}$ Ed. vol 2, Bland & Kirby eds. W.B. Saunders Co, Philadelphia, Pa. pp. 51–74; Wrensch et al., (1992) American Journal of Epidemiology. 135(2):130–41; and Sauter et al., (1997) British Journal of Cancer. 76(4):494–501. Ductal lavage is described in copending patent application Ser. No. 09/067,661 filed Apr. 28, 1998. Cells of the lesion can be retrieved by collecting the ductal fluid that contains some of these cells, e.g., by aspirating the nipple to obtain nipple aspirate fluid, e.g., as described in Petrakis (1993) *Cancer Epidem. Biomarker Prev.* 2:3–10, Petrakis (1986) *Breast Cancer Res. Treat* 8: 7–19, Wrensch et al., (1992) *Am. J. Epidem.* 135:130–141, Wrensch et al., (1990) *Breast Cancer Res Treat* 15: 39–21, and Wrensch et al., (1989) *Cancer Res.* 49: 2168–2174. Also fluid secretions from the nipple can be collected as they spontaneously appear on the nipple surface.

The ductal fluid may be analyzed in situ, i.e., inside the breast and inside the breast duct, e.g., where a particular marker can be introduced into the duct and can be identified from within the breast. In situ testing within the duct is also considered a noninvasive means of examining the ductal epithelial cells. Ductal epithelial cells that are examined by the method of the invention can be examined in situ (i.e., in the duct; e.g., where a marker can bind the cells or a component of the cells in the duct and be identified from within the breast by a tag attached to the marker), or after the ductal epithelial cells have been removed from the breast of the patient by non-invasive means, e.g., as just described. Methods of in situ analysis can include use of such molecular biology tools, methods, and materials as described in e.g., U.S. Pat. Nos. 5,169,774, 5,720,937, 5,677,171, 5,720,954, 5,725,856, 5,770,195, and 5,772,997. Markers to breast cancer and breast precancer described elsewhere and herein may also be used for an in situ analysis of the breast duct.

The ductal fluid is examined to detect the presence of precancerous or cancerous ductal epithelial cells. The fluid sample (comprising ductal epithelial cells) can be analyzed by any effective means for identifying breast precancer or cancer, including e.g., cytological analysis of the cells retrieved or identified. Examination of the ductal epithelial cells can be accomplished by examining useful indicators such as, e.g., the morphology of the cells or cellular contents. The cellular contents can include, e.g., protein, nucleic acid, or other molecular markers in the cells. Cell morphology can serve to establish whether the ductal epithelial cells are normal (i.e., not precancerous or cancerous or having another noncancerous abnormality), precancerous (i.e., comprising hyperplasia, atypical ductal hyperplasia (ADH) or low grade ductal carcinoma in situ (LG-DCIS)) or cancerous (i.e., comprising high grade ductal carcinoma in situ (HG-DCIS), or invasive carcinoma). Analysis of cell contents may serve to establish similar staging as established by morphology, capturing generally a progression of a precancerous or cancerous condition in the cells. Thus, the ductal epithelial cells may be analyzed for other markers, e.g., protein markers, nucleic acid markers, or biochemical markers in the cells or on the cell surfaces or for any marker providing evidence of neoplasia. The ductal epithelial cell can be derived from any part of the breast milk duct, including, e.g., the ductal lumen and/or the terminal ductal lobular unit (TDLU). Cells derived from the TDLU may also have similar stages as found in other luminal ductal epithelial cells not from the TDLU including, e.g., hyperplasia, atypia, in situ carcinoma, and invasive carcinoma.

Cytological assays that can be performed on the cells retrieved from a duct or from nipple aspirate can include e.g., assays described in King et al., *J. Nat'l Cancer Inst* (1983) 71:1115–21, Wrensch et al., (1992) *Am. J. Epidem.* 135: 130–141, Papanicolaou et al., (1958) *Cancer,* 11:377–409 and Goodson W H & King E B, *Chapter 4: Discharges and Secretions of the Nipple,* THE BREAST: COMPREHENSIVE MANAGEMENT OF BENIGN AND MALIGNANT DISEASES (1998) $2^{nd}$ Ed. vol 2, Bland & Kirby eds. W.B. Saunders Co, Philadelphia, Pa. pp. 51–74.

For example, as described in Goodson and King (page 60) atypical hyperplasia presents having cellular abnormalities, increased coarseness of the chromatin and tendency for more single cells as well as groups of cells. With regard to carcinoma in situ, Papanicolaou et al., described cellular abnormalities, e.g., nuclear abnormalities diagnosed by cytology of fluid from nipple secretions containing ductal cells. The cytology of abnormal cells can also be conducted as described in Sartorius et al., (1977) *J. Natl Cancer Inst* 59: 1073–1080. and King et al., (1983) *JNCI* 71(6) 1115–1121. Atypia and carcinoma in situ are widely characterized pathologically, as described in Page et al., (1998) *Mod Pathol* 11(2): 120–8. The ductal fluid can be analyzed by cytological techniques by placing some of the fluid on a slide with a standard cytological stain using a light microscope. The cells can be studied for atypical growth patterns in individual cells and clusters of cells using published methods, including Mouriquand J, (1993) S Karger Pub, "Diagnosis of Non-Palpable Breast Lesions: Ultrasonographically Controlled Fine-Needle Aspiration: Diagnostic and Prognostic Implications of Cytology" (ISBN 3805557477); Kline T S and I K, Pub Igaku-Shoin Medical "Breast: Guides to Clinical Aspiration Biopsy" (LSBN 0896401596; Masood, *American Society of Clinical Pathology:* November 199S, "Cytopathology of the Breast" ISBN 0891893806; and Feldman P S, *American Society of Clinical Pathology,* November 1984, "Fine Needle Aspiration Cytology and Its Clinical Applications: Breast and Lung" ISBN 0891891846.

The aromatase enzyme can be any aromatase enzyme or form of an aromatase enzyme, e.g., as described or targeted in Blankenstein et al., *J. Steroid Biochem Mol Biol* (1999) 69:293–297; Brodie et al., *J. Steroid Biochem Mol Biol* (1999) 69:205–210; Brueggemeier et al., *Cancer Lett* (1999) 40:27–35; Brodie et al., *Breast Cancer Res Treat* (1998) 49 suppl 1:S85–91; and Goss, P E, *Breast Cancer Res Treat* (1998) 49 Suppl 1:S59–65; disc. S73–7. The aromatase activity, can be any detectable or measurable aromatase activity, e.g., detectable aromatase activity described in Magoffin et al., *Ginekol Pol* (1999) 70:1–7; Shenton et al., *Breast Cancer Res Treat* (1998) 49 Supple 1:S101–107; and Santen et al., *Breast Cancer Res. Treat* (1998) 49 Suppl 1:S93–99; disc S109–119. The biproduct of estrogen synthesis can be any metabolite or degradation product of estrogen, including e.g., 2-hydroxyestrone, 4-hydroxyestrone, 16 alpha-hydroxyestrone, 4-hydroxyestradiol, and others e.g., as described in Xu et al., *J. Clin Endocrinol Metab* (1999) 84(11):3914–8. Estrogen biosynthesis is described in U.S. Pat. No. 4,546,098 to Fishman et al. The protein effector acting upstream of estrogen synthesis, can be e.g., any protein involved in or affecting or contributing to the synthesis of estrogen, or which has an effect on estrogen synthesis and which if modulated in some way would in turn modulate estrogen synthesis downstream of the first modulation effect on the first protein effector.

The ductal fluid sample can be further examined for the presence of an elevated level of estrogen or an estrogen metabolite, wherein elevated level is a level above normal. Normal for the purposes herein refers to levels of a marker (e.g., estrogen or estrogen-related marker or other marker) localized in the breast duct fluid. Normal levels can be established across a population, and may be defined within a subpopulation (e.g., by age or other parameter). Normal levels are those levels found in women who are considered healthy and who do not have one or more abnormal ductal epithelial cells. At least 15 endogenous estrogens are known (See, e.g., Xu et al., *J. Clin Enocrinol Metab,* 84(11):3914–8 (1999), including e.g., estradiol and estrone, 16 alpha-hydroxyestrone, 4-hydroxyestradiol, 4-hydroxyestrone, 2-hydroxyestrogens and 4-hydroxyestrogens, and can be measured as described in Xu et al., or by other means standard in the art for detecting hormones of estrogen-like character, e.g., immunohistochemistry, binding assays, antibody detection and the like.

Additionally, the presence of an estrogen receptor on the cell surface of precancerous or cancerous epithelial cell can also be detected. The presence of estrogen receptor can be tested by any standard technique available for detecting the presence of proteins generally in cells. In precancer and some early cancer, it is expected that the estrogen receptor will be positive (i.e., 20% or greater staining by a standard estrogen receptor test). In later cancers and some early cancers, the estrogen receptor may be negative (i.e., less than 20% staining or less in the cells analyzed). Assays for testing for the presence of ER can include standard cytoplasmic protein and/or receptor detection assays provided by standard protocol books, e.g., in Sambrook, 1989, *Molecular Cloning, A Laboratory Manual,* 2d Ed., Cold Spring Harbor Laboratory Press, Cold Spring Harbor, N.Y., and Ausubel et al., *Current Protocols in Molecular Biology,* 1987–1997 *Current Protocols,* 1994–1997 John Wiley and Sons, Inc.). For example, estrogen receptor immunocytochemistry ER-ICA (available from Abbott laboratories, located in Abbott Park, Ill.) can be used to identify and quantify the ER from a sample of breast milk duct fluid in order to establish an ER positive condition of ductal epithelial cells retrieved from the milk duct.

The estrogen activity modulator administered to a patient can comprise e.g., an aromatase inhibitor, an estrogen antagonist, a selective estrogen receptor modulator, or a modulator of a protein effector acting upstream of estrogen synthesis, or any combination of these, e.g., a cocktail of two or more of these agents. All of these may broadly be categorized as estrogen activity modulators. Estrogen activity modulators can include agents that block estrogen activity, either by modulating estrogen, its receptor, or by blocking estrogen synthesis. An estrogen activity modulator can comprise a class of agents selected from the group consisting of a selective estrogen receptor modulator (SERM), an estrogen antagonist, and a modulator of estrogen synthesis. The estrogen activity modulator can be tamoxifen, raloxifene, EM 800, droloxifene, ioxdroxifene, RU 39411, RU 58668, ICI 164384, faslodex, soy, a soy isoflavone, a gonadotropin releasing hormone agonist, or an aromatase inhibitor. An inhibitor of estrogen synthesis is described, e.g., in U.S. Pat. No. 4,546,098. The soy isoflavone can be genistein or daidzein. The aromatase inhibitor (also called an inhibitor of estrogen synthase) can be toremifene, letrozole (CGS 20,269) (Lamb and Atkins, *Drugs,* 56(6):1125–40 (1998), ICI 182,780 (Long et al., *J Steroid Biochem Mol Biol* 67(4):293–304 (1998), fadrozole hydrochloride (CGS 16949A) (Costa et al., *Cancer* 85(1):100–3 (1999), rivizor (also called vorozole) (Goss et al., *Oncology* 56(2):114–21 (1999) and Goss, *Breast Cancer Res Treat* 49 Suppl: S59–65, S73–7 (1998), anastrozole (ZN 1033) (Brodie et al., *J. Steroid Biochem Mol Biol* 69(1–6):205–10 (1999), 4-hydroxyandrostenedione (4-OHA, lentaron or formestane, See, Trunet et al., *J. Steroid Biochem Mol Biol* 61(3–6):241–5 (1997)) (Brodie et al., *J. Steroid Biochem Mol Biol* 69(1–6):205–10 (1999), and rivizor.

Other possible candidate estrogen activity modulators are described in el Khissiin and Leclercq, (1998) *Steroids* 63(11): 565–74; O'Regan et al., (1998) *J Nat'l Cancer Inst* 90(20):1552–8; Favoni and Cupis (1998) *Trends Pharmacol Sci* 19(10): 406–15; Williams, G M (1998) *J Nat'l Cancer Inst* 90:1671; Huynh et al., (1996) *Clin Cancer Res* 2:2037–2042; England and Jordan (1997) *Oncol Res* 9:397–402; Ashby et al., (1997) *Regul Toxicol Pharmacol* 25:226–31, Long et al., (1998) J Steroid Biochem Mol Biol 67:293–304. In addition, estrogen activity modulators obtained from plants or foods can be used, including soy and soy isoflavones, including genistein and daidzein, as described in Xu et al., (1998) *Cancer Epidemiol Biomarkers Prev* 7:1101–8, Charland et al., (1998) *Int J Mol Med* 2:225–228, Franke et al., (1998) *Am J Clin Nutr* 68:1466S–1473S, Kim et al., (1998) *Am J Clin Nutr* 68: 1418S–1425S, Shao et al., (1998) *Cancer Res* 58:4851–7, Shao et al., *Journal of Cellular Biochemistry* 69(1):44–54, 1998; Liggins et al., (1998) *Anal Biochem* 264:1–7, Kinoshita et al., (1998) *Adv Exp Med Biol* 439: 1178–29, and Dees and Kennedy (1998) *Curr Opin Oncol* 10(6):517–522. Estrogen activity modulators that are aromatase inhibitors are described in Mor et al., (1998) *J Steroid Biochem Mol Biol* 67(5–6):403–411; Goss et al., (1999) *Oncology* 56(2):114–121; Coombes (1998) *Recent Results Cancer Res* 152:277–84; Costa et al., (1999) *Cancer* 85:100–3; Long et al., (1998) *J Steroid Biochem Mol Biol* 67(4): 293–304; and Lamb and Adkins (1998) *Drugs* 56(6):1125–40. Gonadotropin hormone releasing agonists (GnRHA) are described at website www.amaassn.org/special/womh/newsline/reuters/03315440.htm (date 4–5–99); and in other publications including Jonat Apr. 5, 1999 (1998) Br J Cancer 78 Suppl 4:5–8; Szamel et al., (1998) *Cancer Chemother Pharmacol* 42(3):241–6; Ciardo et al., (1998) *Minerva Ginecol* 50(1–2):25–29; Nagy et al., (1996) *Proc Natl Acad Sci USA* 93(14):7269–73; Burger et al., (1996) *Eur J Obstet Gynecol Reprod Biol* 67(1):27–33.

The method can further comprise examining the ductal fluid sample to detect one or more presence of precancerous or cancerous ductal epithelial cells; wherein if a precancerous or cancerous ductal epithelial cell is detected, the patient can be a candidate for an action including administration of an estrogen activity modulator, stopping the HRT, reducing the dosage of hormone in the HRT, or switching to a different hormone or agent for treating menopausal symptoms or osteoporosis. Such a patient may also be tested for estrogen, or estrogen receptor in the ductal fluid as described above. And any action to treat such a patient can comprise administration of an estrogen activity modulator, wherein the estrogen activity modulator is administered intraductally to an affected duct or ducts. Where the action comprises administration of an estrogen activity modulator, and the estrogen activity modulator can be, e.g., an aromatase inhibitor, an estrogen antagonist, a selective estrogen receptor modulator, or a modulator of a protein effector acting upstream of estrogen synthesis.

Treatment of a pre-, peri-, menopausal, or postmenopausal woman who has been determined to have one or more precancerous or cancerous ductal epithelial cell (e.g., by methods described herein) and an elevated level of a marker including aromatase enzyme, aromatase activity, a biproduct of estrogen synthesis, or a protein acting upstream of estrogen synthesis in a ductal fluid sample can comprise administering at least one dose of an aromatase inhibitor. Exemplary aromatase inhibitors are listed herein. Normal levels are determined as described elsewhere herein. Administrating the aromatase inhibitor can comprise intraductal delivery of the aromatase inhibitor. The intraductal delivery can comprise accessing the breast duct with a ductal access device and delivering the aromatase inhibitor. The aromatase inhibitor can comprise a time release formulation. Women of pre-, peri-, menopausal or postmenopausal age not determined to have one or more precancerous or cancerous ductal epithelial cell would be subject to further regular monitoring, but would not necessarily be candidates for the treatment described herein.

Treatment of the pre-, peri, or postmenopausal woman who has been determined to have one or more precancerous or cancerous ductal epithelial cell and an elevated level of estrogen or estrogen metabolite in a ductal fluid sample can comprise administering at least one dose of an estrogen activity modulator intraductally. The estrogen activity modulator can be e.g., any listed herein, including e.g., an estrogen antagonist, an aromatase inhibitor, a selective estrogen receptor modulator, a modulator of a protein effector acting upstream of estrogen synthesis, or a cocktail of estrogen activity modulators.

The invention similarly provides a method of screening a woman who has an increased chance of benefiting from postmenopausal hormone replacement therapy (HRT) wherein HRT is contradicted in women having abnormal ductal epithelial cells. Such a woman is determined to benefit from HRT if she requires, e.g., amelioration of menopausal symptoms and/or possibly protection against or treatment for an osteoporotic condition, a heart condition, or any other condition implicated by or believed to be related to reduced systemic estrogen levels in women. Hormone replacement therapy comprises, e.g., administration of estrogen and/or progesterone to the patient. HRT is generally practiced to assuage menopausal symptoms and/or to reduce other health risks or complications associated with women of menopausal age and postmenopausal. The woman can be surgically postmenopausal. The method comprises providing a ductal fluid sample from at least one duct of a breast of the patient, and examining the ductal fluid sample for the presence of a precancerous or cancerous ductal epithelial cell, wherein a patient having one or more precancerous or cancerous ductal epithelial cells is not a candidate for post menopausal HRT. The ductal fluid sample can be examined for an elevated level of a marker including aromatase enzyme, aromatase activity, estrogen, estrogen metabolite, a biproduct of estrogen synthesis, or a protein acting upstream of estrogen synthesis in a ductal fluid. The ductal fluid sample can be further examined for presence of estrogen receptor on the ductal epithelial cells. For a patient who has been determined to have precancerous or cancerous ductal epithelial cells, an increase in one or more such markers indicates a therapy including administration of a lower dosage of hormone in the HRT, close monitoring of markers and ductal epithelial cell changes while the patient is on HRT, selecting an agent for HRT that provides a reduced breast cancer risk, not placing the patient on HRT, or administering an estrogen activity modulator to an affected duct or ducts intraductally. During the monitoring of a patient, when a marker is increased, and the ductal epithelial cells are normal, the patient can be placed on HRT and monitored periodically for changes in marker levels or ductal epithelial cell character. As in previous embodiments of the method, providing the ductal fluid sample can comprise obtaining the sample from the breast; providing the ductal fluid sample can comprise receiving a sample which has been previously obtained; the fluid can be obtained by nipple aspiration or by ductal lavage of at least one milk duct; and the fluid can be collected from a single duct. Examining the ductal fluid can comprise cytological examination of ductal epithelial cells in the sample to determine whether they are precancerous or cancerous, and the cytology can comprise methodologies listed herein. In some circumstances, selecting an agent for HRT that provides a reduced breast cancer risk is directed.

The invention further includes a method of monitoring a postmenopausal woman on hormone replacement therapy (HRT) comprising providing a ductal fluid sample from one or more ducts of a breast of a patient, and examining the ductal fluid sample for a precancerous or cancerous ductal epithelial cells, wherein indicated therapies for such patients include stopping HRT, reducing a dosage of hormone in the HRT, beginning taking an estrogen activity modulator systemically, beginning taking an estrogen activity modulator intraductally, switching to a different drug to reduce menopausal symptoms, and switching to a different drug to reduce bone loss. The method can further comprise examining the ductal fluid sample for presence of estrogen receptor on cancerous or precancerous ductal epithelial cells. The therapy can comprise taking an estrogen activity modulator, and the estrogen activity modulator can be administered intraductally. The estrogen activity modulator can comprise an aromatase inhibitor. The therapy can comprise switching to a different drug (e.g., Fosamax) to ameliorate menopausal symptoms or osteoporosis risk. The method of monitoring can further comprise assaying the ductal fluid for an elevated level of a marker including estrogen, an estrogen metabolite, aromatase enzyme, evidence of aromatase activity, biproducts of estrogen synthesis, or a protein effector acting upstream of estrogen synthesis; wherein an elevated level in one or more markers indicates a therapy including administration of a lower dosage of hormone in the HRT, close monitoring of markers while the patient is on HRT, close monitoring of ductal epithelial cell changes while the patient is on HRT, selecting an agent for HRT that provides a reduced cancer risk, stopping the HRT, or intraductal administration of an estrogen activity modulator to an affected duct or ducts. When a marker is increased, and the ductal epithelial cells are normal, the patient may be directed to remain on HRT and monitored periodically for changes in marker levels and ductal epithelial cells. Upon the discovery of one or more abnormal ductal epithelial cells in a patient determined to benefit from HRT, a different option to treat the bone density loss and abnormal cells may be the most preferred therapy. For example selective estrogen activity modulators may be chosen. Other drugs that may be administered to continue to treat the osteoporosis include alendronate and nasal calcitonin. See, Watts, *Obstet Gynecol Surv* 54(8):532–8 (1999). In addition, at that point in the patient's history, the patient may benefit also from another differently acting estrogen activity modulator, including any available presently. Some may also have the benefit of some reduction in osteoporosis, or additional drugs (like aldendronate and/or nasal calcitonin) may also be administered. The invention further provides a method of treating a peri-, menopausal, or postmenopausal woman for both cancer risk and reduction of menopausal symptoms, osteoporosis, or cardiovascular risk wherein the peri, menopausal, or postmenopausal woman is determined to have an elevated level of a marker including estrogen, an estrogen metabolite, aromatase enzyme, aromatase activity, a biproduct of estrogen synthesis, or a protein acting upstream of estrogen synthesis in a ductal fluid. The therapy comprises systemically administering estrogen hormone, and locally administering an estrogen activity modulator to one or more breast milk ducts in which is identified an increased level of one or more markers. Local administration of an estrogen activity modulator can comprise intraductal administration. The estrogen activity modulator can comprise an estrogen antagonist, an aromatase inhibitor, or a cocktail of estrogen activity modulators. The estrogen activity modulator can be an aromatase inhibitor e.g., torimefene, anastrozole (ZN 1033), letrozole (CGS 20,269), ICI 182, fadrozole hydrochloride (CGS 16949A), rivizor (also called vorozole), or 4-hydroxyandrostenedione (4-OHA, lentaron or formestane). The method can comprise monitoring one or more breast ducts of the patient for precancerous or cancerous ductal epithelial cells at time points including before, during, and after the systemic estrogen administration.

The invention further provides kits for practicing the methods. Thus, kits are provided for screening a woman by retrieving a ductal fluid sample from the breast of the woman, as directed in the methods above, using a device fashioned for that purpose (e.g., a cannula or catheter to access the breast duct and retrieve fluid from the duct). A kit for screening a postmenopausal woman determined to benefit from HRT for precancer or cancer can comprise a device for retrieving a ductal fluid sample from a breast of the woman, and instructions comprising the methods described herein for such screening. A kit for monitoring a postmenopausal woman on HRT for precancer or cancer comprises a device for retrieving a ductal fluid sample from a breast of the woman, and instructions comprising the methods for monitoring described above. A kit for treating a woman who has been determined to have one or more precancerous or cancerous ductal epithelial cell comprising a device for retrieving a ductal fluid sample from a breast of the woman, and instructions comprising the methods of treating these patients as described above. Such kits can further comprise a therapeutic agent for intraductal delivery or other local delivery to a patient, and the therapeutic agent can comprise an estrogen activity modulator. The estrogen activity modulator can comprise an aromatase inhibitor. The therapeutic agent can be delivered by intraductal delivery to a patient. The instructions can comprise a treatment algorithm for determining an appropriate dosage and administration schedule of the agent. The algorithm can comprise e.g., an identified drug or cocktail of drugs, a dosage amount, frequency of administration, and a monitoring schedule for the patient.

EXAMPLES

1. Screening a Postmenopausal Women Experiencing Symptoms of Osteoporosis for HRT A 50-year old women post-hysterectomy is tested for low bone density and found to have low bone density. Several ducts in her right and left breasts were lavaged and the fluid kept separate for separate analysis. No abnormal ductal epithelial cells were detected after cytological analysis of the fluid. She is scheduled for annual lavages of her breast ducts during the time that she is place on HRT of a combined estrogen/progestin formulation.

2. Monitoring Woman "A" on HRT for Continued Suitability for the Therapy

A 65 year-old women who has been receiving postmenopausal HRT for 6 years is tested for abnormal ductal epithelial cells by ductal lavage of 3 fluid-yielding ducts (2 on her right breast and 1 on her left breast). The fluid yielding ducts are identified by nipple aspiration of both breasts, and immediately following the nipple aspiration procedure, the fluid yielding ducts were lavaged. All fluid-yielding ducts present with ductal hyperplasia. The dosage of estrogen is lowered and HRT is continued, and the ductal fluid retrieved and analyzed in 6 months.

3. Monitoring Women "B" on HRT for Continued Suitability for the Therapy

Woman "B" (age 57) has been on postmenopausal HRT for 7 years after having a hysterectomy at age 50. Her propensity for low bone density is reduced since commencing the estrogen/progestin therapy recommended by her physician. At age 57 both breasts are subjected to nipple aspiration which procedure identified one fluid-yielding duct on her right breast. This duct is lavaged and the fluid retrieved is analyzed by cytology. The ductal fluid sample indicates no ductal epithelial cell abnormalities. Her treating physician directs that the estrogen/progestin therapy continue at the established dosage and directs that the patient be monitored for low bone density at appropriate time intervals.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of determining if a patient should undergo postmenopausal hormone replacement therapy (HRT) based on results of a ductal fluid sample analysis, said method comprising:
    providing a ductal fluid sample from at least one duct of a breast of the patient, said ductal fluid sample being obtained by nipple aspiration or by ductal lavage of at least one milk duct;
    examining the ductal fluid sample for the presence of a precancerous or cancerous ductal epithelial cell; and
    identifying whether a patient should undergo hormone replacement therapy in response to detecting or not detecting the presence of precancerous or cancerous ductal epithelial cell in the ductal fluid sample.

2. A method as in claim 1, wherein the precancerous ductal epithelial cell comprises a cell at a stage selected from the group consisting of ductal hyperplasia, atypical ductal hyperplasia, and low grade ductal carcinoma in situ (LG-DCIS).

3. A method as in claim 1, wherein the cancerous ductal epithelial cell comprises a cell at a stage selected from the group consisting of high grade ductal carcinoma in situ (HG-DCIS) and invasive carcinoma.

4. A method as in claim 1, further comprising determining in the sample a level of a marker selected from the group consisting of aromatase enzyme, aromatase activity, estrogen, estrogen metabolite, a biproduct of estrogen synthesis, and a protein acting upstream of estrogen synthesis in a ductal fluid, wherein a level above normal indicates an increased risk for developing cancer or precancer in the breast.

5. A method as in claim 1 or 4, further comprising examining the cancerous or precancerous ductal epithelial cells to detect the presence of an estrogen receptor, wherein the presence of the estrogen receptor indicates that the cell is hormone responsive.

6. A method as in claim 1, wherein the patient is surgically postmenopausal.

7. A method as in claim 4 or 5, further comprising detecting precancerous or cancerous ductal epithelial cells in the sample, wherein the presence of precancerous or cancerous ductal epithelial cells indicates the patient has an increased chance of benefiting from at least one of administration of a lower dosage of hormone in the HRT, close monitoring of markers and ductal epithelial cell changes while the patient is on HRT, selecting an agent for HRT that provides a reduced breast cancer risk, not placing the patient on HRT, and administering an estrogen activity modulator to an affected duct or ducts intraductally.

8. A method as in claim 7, wherein when a marker is increased, and the ductal epithelial cells are normal, the patient is placed on HRT and monitored periodically for changes in marker levels and ductal epithelial cells.

9. A method as in claim 1, wherein providing the ductal fluid sample comprises obtaining the sample from the breast.

10. A method as in claim 1, wherein providing the ductal fluid sample comprises receiving a sample which has been previously obtained.

11. A method as in claim 1, wherein the fluid is collected from a single duct.

12. A method as in claim 1, wherein examining the ductal fluid comprises cytological examination of ductal epithelial cells in the sample to determine whether they are precancerous or cancerous.

13. method of screening a patient for postmenopausal hormone replacement therapy (HRT), said method comprising the steps of:

introducing a portion of a catheter into a breast duct of the patient;

performing ductal lavage including the step of retrieving biological material from within the breast duct through said introduced portion of the catheter;

obtaining a ductal fluid sample from said breast duct;

examining the ductal fluid sample for the presence of at least one precancerous or cancerous ductal epithelial cell; and wherein HRT is contradistinguished if the patient has a precancerous or cancerous ductal epithelial cell in the ductal fluid sample.

14. The method of claim 13 wherein said step of performing ductal lavage also includes the step of infusing a fluid into said breast duct through said catheter.

15. The method of claim 13 further including the step of identifying if the patient should undergo hormone replacement therapy in response to results of the examining step.

16. A method of screening a patient for postmenopausal hormone replacement therapy (HRT), said method comprising the steps of:

introducing a portion of a catheter into a breast duct of a patient;

performing ductal lavage on said breast duct including the steps of infusing a fluid into the duct through said introduced portion of the catheter and obtaining a ductal fluid sample from a breast duct of the patient including retrieving biological material from within the breast duct through said introduced portion of the catheter;

examining the ductal fluid sample for the presence of at least one precancerous ductal epithelial cell; and wherein HRT is contradistinguished if the patient has a precancerous ductal epithelial cell in the ductal fluid sample.

17. The method of claim 16 further including the step of identifying if the patient should undergo hormone replacement therapy in response to results of the examining step.

* * * * *